(12) United States Patent
Vilokkinen et al.

(10) Patent No.: US 11,490,961 B2
(45) Date of Patent: Nov. 8, 2022

(54) METHOD AND SYSTEM FOR CONFIGURING BIOMEDICAL LASER

(71) Applicant: Modulight Corporation, Tampere (FI)

(72) Inventors: Ville Vilokkinen, Tampere (FI); Petteri Uusimaa, Tampere (FI); Seppo Orsila, Ylojarvi (FI)

(73) Assignee: Modulight Corporation, Tampere (FI)

( * ) Notice: Subject to any disclaimer, the term of this patent is extended or adjusted under 35 U.S.C. 154(b) by 339 days.

(21) Appl. No.: 16/927,201

(22) Filed: Jul. 13, 2020

(65) Prior Publication Data

US 2020/0337769 A1 Oct. 29, 2020

Related U.S. Application Data

(63) Continuation-in-part of application No. 15/703,238, filed on Sep. 13, 2017, now abandoned.

(51) Int. Cl.
| | |
|---|---|
| *A61B 18/20* | (2006.01) |
| *A61B 5/00* | (2006.01) |
| *A61N 5/06* | (2006.01) |
| *A61F 9/008* | (2006.01) |
| *A61B 17/00* | (2006.01) |
| *A61B 18/00* | (2006.01) |
| *A61N 5/067* | (2006.01) |

(52) U.S. Cl.
CPC ............ *A61B 18/20* (2013.01); *A61B 5/0071* (2013.01); *A61F 9/00821* (2013.01); *A61N 5/062* (2013.01); *A61B 2017/00057* (2013.01); *A61B 2017/00154* (2013.01); *A61B 2018/00702* (2013.01); *A61B 2018/00958* (2013.01); *A61N 5/067* (2021.08)

(58) Field of Classification Search
None
See application file for complete search history.

(56) References Cited

U.S. PATENT DOCUMENTS

| | | | |
|---|---|---|---|
| 2004/0092919 A1* | 5/2004 | Ritchie .................. | A61B 18/22 606/34 |
| 2006/0274794 A1* | 12/2006 | Watanabe ............ | B23K 26/707 372/33 |
| 2014/0272771 A1* | 9/2014 | Boutoussov .......... | A61G 15/14 433/29 |

\* cited by examiner

*Primary Examiner* — Ankit D Tejani
(74) *Attorney, Agent, or Firm* — Ziegler IP Law Group, LLC

(57) ABSTRACT

A method for re-configuring a biomedical laser device. The biomedical laser device is pre-configured to be operable in one or more operational modes, and is provided with set of operational parameters that are employed for at least one of: given medical procedure, given medical treatment, activation of given drug, illumination of given dye. The method includes collecting information indicative of light output properties of biomedical laser device measured during given operational mode; detecting deviation in measured light output properties with respect to predefined light output properties for given operational mode; determining new set of operational parameters that are to be employed for at least one of: new medical procedure, new medical treatment, activation of new drug, illumination of new dye; and sending new set of operational parameters to biomedical laser device for re-configuring biomedical laser device to be operable in a new operational mode.

18 Claims, 4 Drawing Sheets

METHOD AND SYSTEM FOR CONFIGURING BIOMEDICAL LASER

CROSS-REFERENCE TO RELATED APPLICATIONS

This application is a continuation-in-part of U.S. patent application Ser. No. 15/703,238, titled "METHOD AND SYSTEM FOR CONFIGURING BIOMEDICAL LASER" and filed on Sep. 13, 2017, which is incorporated herein by reference.

TECHNICAL FIELD

The present disclosure relates generally to biomedical lasers; and more specifically, to methods for re-configuring biomedical laser devices. The present disclosure also relates to systems for re-configuring biomedical laser devices.

BACKGROUND

Nowadays, laser devices are increasingly being used for several biomedical applications. Though prevalent in ophthalmology and dermatology, laser devices have also found use in surgical procedures, cancer diagnosis and treatment, biomedical imaging, gene sequencing and the like. Therefore, in many biomedical applications, laser devices have become a mainstay and are quickly replacing conventional tools. This is possible since operational parameters (such as wavelength of emitted light, intensity of the emitted light, and the like) of laser devices can be configured for various biomedical applications.

Due to high risk and precision requirements associated with biomedical applications, laser devices used in medicine (or biomedical laser devices) are required to operate within precise limits. The slightest deviation from the approved precise limits may cause severe, and in some cases fatal, injuries or cause wrong biomedical diagnosis, treatment or analysis. Moreover, light emitting sources and other components (such as optical couplers, light guides, and the like) of the biomedical laser devices may often deteriorate or break down over time. This leads to the biomedical laser devices becoming ineffective and/or unsafe for their original intended biomedical applications.

Therefore, several techniques are being devised nowadays to monitor operation of the biomedical laser devices. However, these techniques are not sufficiently well-developed, and are often unable to detect fluctuations and/or anomalies in the operation of the biomedical laser devices. There is still heavy reliance on manual on-site monitoring of the operation of the biomedical laser devices (for example, by users of the biomedical laser devices). Remote monitoring of the operation of the biomedical laser devices is even more challenging than on-site monitoring owing to challenges associated with access of operation data and accuracy of the operation data.

Moreover, the biomedical laser devices may require re-configuration for several reasons, such as becoming ineffective and/or unsafe for their original intended biomedical applications, requirement of using the biomedical laser device for new biomedical applications, and the like. However, re-configuring the biomedical laser devices is quite challenging. Such re-configuration requires effective monitoring and control of the biomedical laser devices, which is not optimally possible using existing techniques. Manual re-configuration involves considerable data analysis and is highly prone to human errors. Remote re-configuration of the operation of the biomedical laser devices is even more challenging than on-site re-configuration, as it involves challenges such unavailability of accurate monitoring data, difficulties in accessing the biomedical laser devices, difficulties in controlling the biomedical laser devices and the like.

Therefore, in light of the foregoing discussion, there exists a need to overcome the aforementioned drawbacks associated with monitoring and re-configuration of biomedical laser devices.

SUMMARY

The present disclosure seeks to provide a method for re-configuring a biomedical laser device. The present disclosure also seeks to provide a system for re-configuring a biomedical laser device. The present disclosure also seeks to provide another method for re-configuring a biomedical laser device. The present disclosure seeks to provide a solution to the existing problems associated with monitoring and re-configuration of biomedical laser devices. An aim of the present disclosure is to provide a solution that overcomes at least partially the problems encountered in prior art, and provides efficient, reliable, easy to implement methods and system for re-configuring a biomedical laser device.

In one aspect, an embodiment of the present disclosure provides a method for re-configuring a biomedical laser device, wherein the biomedical laser device is pre-configured to be operable in one or more operational modes, the biomedical laser device being provided with a set of operational parameters to be employed in a given operational mode of the one or more operational modes, wherein the set of operational parameters are employed for at least one of: a given medical procedure, a given medical treatment, an activation of a given drug, an illumination of a given dye, the method comprising:

collecting, from the biomedical laser device, information indicative of light output properties of the biomedical laser device measured during the given operational mode;

detecting a deviation in the measured light output properties with respect to predefined light output properties for the given operational mode;

determining, based on the detected deviation, a new set of operational parameters that are to be employed for at least one of: a new medical procedure, a new medical treatment, an activation of a new drug, an illumination of a new dye; and sending the new set of operational parameters to the biomedical laser device for re-configuring the biomedical laser device to be operable in a new operational mode, wherein the new set of operational parameters are employed in the new operational mode.

In another aspect, an embodiment of the present disclosure provides a system for re-configuring a biomedical laser device, the system comprising a server arrangement coupled in communication with the biomedical laser device, wherein the biomedical laser device is pre-configured to be operable in one or more operational modes, the biomedical laser device being provided with a set of operational parameters to be employed in a given operational mode of the one or more operational modes, wherein the set of operational parameters are to be employed for at least one of: a given medical procedure, a given medical treatment, an activation of a given drug, an illumination of a given dye, wherein the server arrangement is configured to:

collect, from the biomedical laser device, information indicative of light output properties of the biomedical laser device measured during the given operational mode;

detect a deviation in the measured light output properties with respect to predefined light output properties for the given operational mode;

determine, based on the detected deviation, a new set of operational parameters that are to be employed for at least one of: a new medical procedure, a new medical treatment, an activation of a new drug, an illumination of a new dye; and send the new set of operational parameters to the biomedical laser device for re-configuring the biomedical laser device to be operable in a new operational mode, wherein the new set of operational parameters are to be employed in the new operational mode.

In yet another aspect, an embodiment of the present disclosure provides a method for re-configuring a biomedical laser device, wherein the biomedical laser device is pre-configured to be operable in one or more operational modes, the biomedical laser device being provided with a set of operational parameters to be employed in a given operational mode of the one or more operational modes, wherein the set of operational parameters are employed for at least one of: a given medical procedure, a given medical treatment, an activation of a given drug, an illumination of a given dye, the method comprising:

measuring light output properties of the biomedical laser device during the given operational mode;

sending, to a server arrangement, information indicative of the measured light output properties for the given operational mode; and receiving, from the server arrangement, a new set of operational parameters that are to be employed for at least one of: a new medical procedure, a new medical treatment, an activation of a new drug, an illumination of a new dye; and re-configuring the biomedical laser device to be operable in a new operational mode, wherein the new set of operational parameters are employed in the new operational mode.

Embodiments of the present disclosure substantially eliminate or at least partially address the aforementioned problems in the prior art, and enable efficient and reliable re-configuration of the biomedical laser device.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
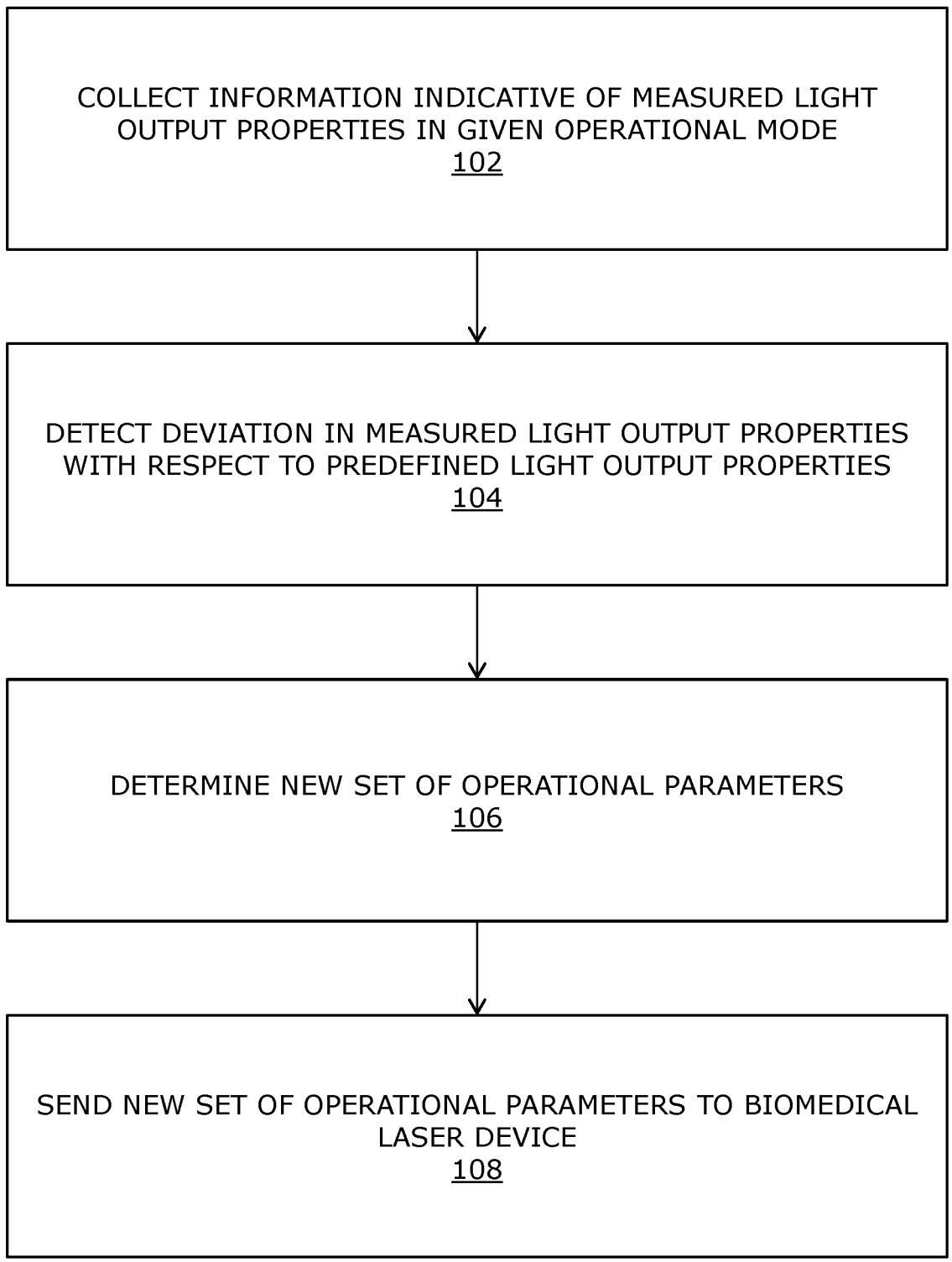
FIG. 1 illustrates steps of a method for re-configuring a biomedical laser device, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides a method for re-configuring a biomedical laser device, wherein the biomedical laser device is pre-configured to be operable in one or more operational modes, the biomedical laser device being provided with a set of operational parameters to be employed in a given operational mode of the one or more operational modes, wherein the set of operational parameters are employed for at least one of: a given medical procedure, a given medical treatment, an activation of a given drug, an illumination of a given dye, the method comprising:

collecting, from the biomedical laser device, information indicative of light output properties of the biomedical laser device measured during the given operational mode;

detecting a deviation in the measured light output properties with respect to predefined light output properties for the given operational mode;

determining, based on the detected deviation, a new set of operational parameters that are to be employed for at least one of: a new medical procedure, a new medical treatment, an activation of a new drug, an illumination of a new dye; and sending the new set of operational parameters to the biomedical laser device for re-configuring the biomedical laser device to be operable in a new operational mode, wherein the new set of operational parameters are employed in the new operational mode.

In another aspect, an embodiment of the present disclosure provides a system for re-configuring a biomedical laser device, the system comprising a server arrangement coupled in communication with the biomedical laser device, wherein the biomedical laser device is pre-configured to be operable in one or more operational modes, the biomedical laser device being provided with a set of operational parameters to be employed in a given operational mode of the one or more operational modes, wherein the set of operational parameters are to be employed for at least one of: a given medical procedure, a given medical treatment, an activation of a given drug, an illumination of a given dye, wherein the server arrangement is configured to:

- collect, from the biomedical laser device, information indicative of light output properties of the biomedical laser device measured during the given operational mode;
- detect a deviation in the measured light output properties with respect to predefined light output properties for the given operational mode;
- determine, based on the detected deviation, a new set of operational parameters that are to be employed for at least one of: a new medical procedure, a new medical treatment, an activation of a new drug, an illumination of a new dye; and
- send the new set of operational parameters to the biomedical laser device for re-configuring the biomedical laser device to be operable in a new operational mode, wherein the new set of operational parameters are to be employed in the new operational mode.

In yet another aspect, an embodiment of the present disclosure provides a method for re-configuring a biomedical laser device, wherein the biomedical laser device is pre-configured to be operable in one or more operational modes, the biomedical laser device being provided with a set of operational parameters to be employed in a given operational mode of the one or more operational modes, wherein the set of operational parameters are employed for at least one of: a given medical procedure, a given medical treatment, an activation of a given drug, an illumination of a given dye, the method comprising:

- measuring light output properties of the biomedical laser device during the given operational mode;
- sending, to a server arrangement, information indicative of the measured light output properties for the given operational mode; and
- receiving, from the server arrangement, a new set of operational parameters that are to be employed for at least one of: a new medical procedure, a new medical treatment, an activation of a new drug, an illumination of a new dye; and
- re-configuring the biomedical laser device to be operable in a new operational mode, wherein the new set of operational parameters are employed in the new operational mode.

The present disclosure provides the aforementioned methods and the aforementioned system for re-configuring the biomedical laser device. The methods described herein are easy to implement and allows for accurate and effective re-configuration of the biomedical laser device. Beneficially, the disclosed methods and system enable remote monitoring and re-configuration of the biomedical laser device. A processor of the biomedical laser device facilitates the aforesaid remote monitoring and re-configuration by providing the system with access to accurate operation data (for example, the information indicative of the measured light output properties) of the biomedical laser device. Moreover, the processor facilitates the system to control the biomedical laser device, by employing the new set of operational parameters sent by the server arrangement for re-configuring the biomedical laser device. The server arrangement employs effective analytical techniques to process the operation data to determine safe and/or effective new set of operational parameters for re-configuration of the biomedical laser device. Beneficially, such efficient remote monitoring and re-configuration of the biomedical laser device enhances utility and performance thereof.

Throughout the present disclosure, the term "biomedical laser device" refers to a device (or an equipment) that produces laser light for purpose of biomedical applications (namely, biomedical diagnosis, biomedical treatments, biomedical procedures, biomedical imaging, and the like). Examples of such biomedical applications include, but are not limited to, cosmetic procedures, surgical procedures, illumination of dyes, drug activation, and dental or ophthalmic treatments. It will be appreciated that the biomedical laser device is required to be configured differently for different biomedical applications. Over time and use, performance of the biomedical laser device may vary, thereby requiring the biomedical laser device to be re-configured for limited or different biomedical applications as compared to original intended applications of the biomedical laser device.

Optionally, the biomedical laser device comprises a laser light emitter for emitting laser light, a light guide optically coupled to the laser light emitter via a light coupling arrangement, and a processor coupled to the laser light emitter. These components of the biomedical laser device are described later in more detail. The term "processor" refers to hardware, software, firmware or a combination of these. The processor facilitates both pre-configuration of the biomedical laser device and the re-configuration of the biomedical laser device. Optionally, the processor comprises a communication module. Optionally, the processor further comprises a memory module.

The biomedical laser device is coupled in communication with the server arrangement. Optionally, the processor of the biomedical laser device communicates with the server arrangement and facilitates the re-configuration of the biomedical laser device. The server arrangement is a part of the system, wherein the system implements the method according to the first aspect. Throughout the present disclosure, the term "server arrangement" refers to an arrangement of at least one server that, when operated, performs the aforementioned steps of the method according to the first aspect. The server arrangement is remote from the biomedical laser device. The biomedical laser device is coupled in communication with the server arrangement, either directly, or via a communication network. The communication network could be an individual network, or a collection of individual networks that are interconnected with each other to function as a single large network. The communication network may be wired, wireless, or a combination thereof. Examples of the individual networks include, but are not limited to, Local Area Networks (LANs), Wide Area Networks (WANs), Metropolitan Area Networks (MANs), the Internet, radio networks, telecommunication networks, and Worldwide Interoperability for Microwave Access (WiMAX) networks.

It will be appreciated that the server arrangement can be implemented in several ways. In an example, the server arrangement could be implemented as a single server. In another example, the server arrangement could have a distributed architecture wherein the server arrangement comprises a plurality of servers. In yet another example, server arrangement could be implemented by way of a cloud server arrangement.

The biomedical laser device is pre-configured to be operable in one or more operational modes. In some implementations, the biomedical laser device is pre-configured to be operable in a single operational mode, whereas in other implementations, the biomedical laser device is pre-configured to be operable in a plurality of operational modes. Throughout the present disclosure, the term "operational mode" refers to a specific mode of operation of the biomedical laser device. A given operational mode is employed for at least one of: a given medical procedure, a given medical treatment, an activation of a given drug, an illumination of a given dye. The "one or more operational modes" of the biomedical laser device may simply be understood to be "one or more modalities" of the biomedical laser device.

It will be appreciated that the biomedical laser device may be pre-configured to be operable in the one or more operational modes, for one or more biomedical applications. The one or more operational modes are employed for the one or more biomedical applications. As an example, the biomedical laser device may be pre-configured to be operable in two operational modes, for two biomedical applications. The two biomedical applications may, for example, be photodynamic therapy and photocoagulation. In such an example, the two operational modes may be M1 and M2, wherein the operational mode M1 may be employed for photodynamic therapy and the operational mode M2 may be employed for photocoagulation.

It will be appreciated that the set of operational parameters to be employed in the given operational mode is provided during pre-configuration of the biomedical laser device. The pre-configuration of the biomedical laser device could be performed during manufacturing or during installation at a facility. Optionally, pre-configuring the biomedical laser device to operate in the one or more operational modes automatically provides one or more sets of operational parameters corresponding to the one or more operational modes.

Optionally, the set of operational parameters to be employed in the given operational mode is provided by a trained biomedical practitioner. Optionally, in this regard, the trained biomedical practitioner inputs the set of operational parameters at a computing device coupled to the biomedical laser device. In some implementations, the computing device is integrated with the biomedical laser device, whereas in other implementations, the computing device is separate from the biomedical laser device. Optionally, the computing device comprises the processor. Examples of the computing device include, but are not limited to, a desktop computer, a laptop computer, and a tablet computer.

Throughout the present disclosure, the term "operational parameter" refers to an operational characteristic of the biomedical laser device. The set of operational parameters to be employed in the given operational mode define a set of operational characteristics of the biomedical laser device in the given operational mode. It will be appreciated that the set of operational parameters are directly related to the one or more biomedical applications for which the biomedical laser device is pre-configured.

Optionally, the set of operational parameters comprises at least one of: a target wavelength, a target energy output of laser light emitted during the given operational mode. These operational parameters pertain to required output characteristics of the laser light emitted during the given operational mode.

Referring to the aforesaid example wherein the biomedical laser device is pre-configured to be operable in the two operational modes M1 and M2, a set S1 of operational parameters to be employed in the operational mode M1 may comprise a target wavelength of X1 nanometer and E1 target energy output of laser light emitted during the operational mode M1, whereas a set S2 of operational parameters to be employed in the operational mode M2 may comprise a target wavelength of X2 nanometer and E2 target energy output of laser light emitted during the operational mode M2. The set S1 of operational parameters is employed for photodynamic therapy and the set S2 of operational parameters is employed for photocoagulation. Beneficially, such a biomedical laser device may be configured to support multiple biomedical applications or modalities that can be activated remotely by calling the operational parameters of each application.

Optionally, the set of operational parameters further comprises at least one of: a current input for operation of the biomedical laser device, a voltage input for operation of the biomedical laser device, an operating temperature of the biomedical laser device. These operational parameters pertain to required drive characteristics for the biomedical laser device during the given operational mode.

Optionally, when the biomedical laser device is operated in the given operational mode, the processor is configured to control operation of the laser light emitter to emit the laser light in accordance with the set of operational parameters. Optionally, the processor provides to the laser light emitter at least one of: the current input, the voltage input, the operating temperature, the target wavelength, the target energy output.

In an embodiment, the biomedical laser device is operated continuously using the set of operational parameters. In such an instance, the biomedical laser device is operated to emit laser light without interruption, for a predetermined period of time. Optionally, in such an instance, the set of operational parameters is constant over the predetermined period of time.

In another embodiment, the biomedical laser device is operated as a series of pulses using the set of operational parameters. In such an instance, the biomedical laser device is operated to emit laser light at periodic time instants. Furthermore, a time duration between two periodic time instants may comprise a first time period and a second time period, wherein the biomedical laser device is operable to emit laser light during the first time period and the biomedical laser device is switched off during the second time period. Beneficially, the biomedical laser device may be operated as the series of pulses for soft tissue surgery, for prevention of necrosis or other unwanted tissue deformation. It will be appreciated that emission of laser light in such a pulsed manner prevents overheating of tissues surrounding a target tissue by allowing for the tissues to cool down during the second time duration (when the biomedical laser device is switched off). In another application, the pulsing of laser light may ensure efficient drug activation or resulting treatment affect through a precise timing of a biochemical process.

The server arrangement collects, from the biomedical laser device, the information indicative of light output properties of the biomedical laser device measured during the given operational mode. In this way, the server arrangement remotely monitors operation of the biomedical laser device during the given operational mode. The "light output properties" of the biomedical laser device refer to properties (namely characteristics) of laser light emitted from the laser light emitter of the biomedical laser device. The measured light output properties are indicative of a currently available output parameter space of the biomedical laser device.

Optionally, the information indicative of the measured light output properties of the biomedical laser device during the given operational mode comprises sensor data measured by a light sensing arrangement during the given operational mode. Said sensor data is highly accurate and reliable. Measurement of the light output properties of the biomedical laser device, using the light sensing arrangement, is described later in detail.

Optionally, the measured light output properties comprise at least one of: a wavelength, a spectrum, an energy, a pulse energy, an optical power, a pulse form factor of laser light emitted during the given operational mode. These light output properties are measured whilst the biomedical laser device is operating in the given operational mode.

In an example, the optical power of the emitted light during the given operational mode of the biomedical laser device may be measured to be up to 5 watts, thereby indicating that a currently available output power space of the biomedical laser device has a range of 0 watts to 5 watts.

In another example, the measured light output properties may comprise a wavelength of the laser light emitted during the given operational mode, wherein the wavelength is equal to 750 nanometres.

Optionally, the step of collecting the information indicative of the measured light output properties is performed periodically. In other words, the server arrangement remotely monitors the biomedical laser device periodically. Such periodic remote monitoring facilitates efficient and timely re-configuration of the biomedical laser device in case of any operational issues or faults.

In an embodiment, the step of collecting the information indicative of the measured light output properties is performed periodically, after equal time intervals. In another embodiment, the step of collecting the information indicative of the measured light output properties is performed periodically, after unequal time intervals. It will be appreciated that a given time interval may be of the order of microseconds, milliseconds, seconds, minutes, hours, and the like.

The server arrangement detects the deviation in the measured light output properties with respect to the predefined light output properties for the given operational mode. Herein, the term "predefined light output properties" for the given operational mode refer to expected light output properties of the biomedical laser device for the given operational mode, wherein the expected light output properties are pre-defined for the given operational mode. The predefined light output properties serve as reference properties that are associated with a normal operation of the biomedical laser device. The predefined light output properties for the given operational mode correspond to the set of operational parameters that are employed in the given operational mode. It will be appreciated that deviations in the measured light output properties with respect to the predefined light output properties for the given operational mode are undesirable, as such deviations are indicative of undesired errors in the operation of the biomedical laser device. The deviations in the measured light output properties with respect to the predefined light output properties may occur due to malfunctioning of the biomedical laser device, modification of the biomedical laser device, wear and tear of the biomedical laser device, and the like.

Optionally, the predefined light output properties comprise at least one of: a reference wavelength, a reference range of wavelengths, a reference spectrum, a reference range of spectrum, a reference energy, a reference range of energies, a reference pulse energy, a reference range of pulse energies, a reference optical power, a reference range of optical powers, a reference pulse form factor, a reference range of pulse form factors predefined for laser light emitted during the given operational mode.

Optionally, detecting the deviation in the measured light output properties with respect to the predefined light output properties for the given operational mode comprises comparing the measured light output properties with the predefined light output properties for the given operational mode. The deviation in a measured light output property with respect to a predefined light output property is detected when: a value of the measured light output property is not equal to a reference value of the predefined light output property, and/or a value of the measured light output property lies outside a reference range of the predefined light output property. The reference range is an acceptable tolerance limit about the reference value of the predefined light output property, when the biomedical laser device operates normally. It will be appreciated that the deviation may occur due to instability of the biomedical laser device. The deviation may indicate that the biomedical laser device is no longer suitable to operate in the given operational mode and may require either: recalibration of optical power or energy to produce the predefined wavelength, or re-configuration to operate in a new operational mode.

In an example, a measured wavelength of the emitted laser light may be equal to 720 nanometres, whereas the reference wavelength of the emitted laser light is 600 nanometres. Clearly, in such an example, values of the measured wavelength and the reference wavelength are unequal. In such a case, an amount of deviation in the measured wavelength with respect to the reference wavelength is 20 percent.

In another example, a measured energy (per photon) of the emitted laser light may be equal to 3 electron volts (eV), whereas a reference range of energies (per photon) may be from 0.5 eV to 2 eV. In such an example, the deviation in the measured energy with respect to reference range of energies is detected, as the value of the measured energy lies outside of the reference range of energies.

The server arrangement determines, based on the detected deviation, the new set of operational parameters that are to be employed for at least one of: the new medical procedure, the new medical treatment, an activation of the new drug, an illumination of the new dye. The new set of operational parameters are different from the set of operational parameters for the given operational mode. It will be appreciated that the new set of operational parameters are determined to be employed for re-configuration of the biomedical laser device. The new set of operational parameters are intended for a different or additional biomedical application than an originally intended biomedical application. The new set of operational parameters are determined since the detected deviation is indicative of suboptimal operation of the biomedical laser device in the given operational mode. Moreover, the new set of operational parameters are accurate as they are determined based on the detected deviation, and enable optimal operation of the biomedical laser device in the new operational mode.

The term "new medical procedure" used herein refers to a medical procedure that has been newly invented in medical society or an existing medical procedure that has been newly approved for use by authorities (for example, at a geographical location where the biomedical laser device is installed). Likewise, the term "new medical treatment" used herein refers to a medical treatment that has been newly invented in medical society or an existing medical treatment that has been newly approved for use by authorities. The term "new drug" used herein refers to a drug that has been newly invented in medical society or an existing drug that has been newly approved for use by authorities. Similarly, the term "new dye" used herein refers to a dye that has been newly invented in medical society or an existing dye that has been newly approved for use by authorities.

Optionally, the new set of operational parameters comprises at least one of: a new target wavelength, a new target energy output of laser light emitted during the new operational mode. These operational parameters pertain to required output characteristics of the laser light emitted during the new operational mode.

Referring to an earlier example wherein the amount of deviation in the measured wavelength (720 nanometres) with respect to the reference wavelength (600 nanometres) was 20 percent, the new set of operational parameters may comprise a new target wavelength equal to 725 nanometres.

Optionally, the new set of operational parameters further comprises at least one of: a new current input for operation of the biomedical laser device, a new voltage input for operation of the biomedical laser device, a new operating temperature of the biomedical laser device. These new operational parameters pertain to required drive characteristics for the biomedical laser device during the new operational mode.

The server arrangement sends the new set of operational parameters to the biomedical laser device for re-configuring the biomedical laser device to be operable in the new operational mode, wherein the new set of operational parameters are to be employed in the new operational mode. Optionally, the server arrangement sends the new set of operational parameters to the processor of the biomedical laser device.

The biomedical laser device may be re-configured with the new operational mode (that employs the new set of operational parameters) based on:
new requirements from medical device regulations or approvals, and/or
a new approved treatment protocol or indication.

The processor of the biomedical laser device, upon receiving the new set of operational parameters corresponding to the new operational mode, re-configures the biomedical laser device to be operable in the new operational mode. The processor employs the new set of operational parameters in the new operational mode, to control operation of the biomedical laser device according to the new set of operational parameters. Upon being re-configured to operate in the new operational mode, the biomedical laser device is operated in accordance with the new set of operational parameters, for one or more biomedical applications.

Optionally, the processor of the biomedical laser device is configured to control operation of the laser light emitter to emit the laser light in accordance with the new set of operational parameters. Optionally, the processor provides at least one of: the new current input, the new voltage input, the new operating temperature for operation of the biomedical laser device, to the laser light emitter.

Optionally, the method according to the first aspect, further comprises:
collecting, from the biomedical laser device, information indicative of light output properties of the biomedical laser device measured during the new operational mode;
detecting whether or not the measured light output properties deviate from predefined light output properties for the new operational mode;
sending, to the biomedical laser device, a notification indicating a successful reconfiguration of the biomedical laser device when the measured light output properties do not deviate from the predefined light output properties for the new operational mode; and
sending, to the biomedical laser device, a notification indicating an unsuccessful reconfiguration of the biomedical laser device when the measured light output properties deviate from the predefined light output properties for the new operational mode.

In this regard, the biomedical laser device is remotely tested to check for its suitability for use in at least one of: the new medical procedure, the new medical treatment, the activation of the new drug, the illumination of the new dye.

Optionally, the information indicative of the measured light output properties of the biomedical laser device during the new operational mode comprises sensor data measured by the light sensing arrangement during the new operational mode. Moreover, optionally, detecting the deviation in the measured light output properties with respect to the predefined light output properties for the new operational mode comprises comparing the measured light output properties with the predefined light output properties for the new operational mode.

It will be appreciated that sending the notification indicating the successful reconfiguration of the biomedical laser device or the notification indicating the unsuccessful reconfiguration of the biomedical laser device is an efficient way of informing a user of the biomedical laser device about current re-configuration status of the biomedical laser device. The user of the biomedical laser device may, for example, be the trained biomedical practitioner, a biomedical researcher, and the like. The notification enables the user to make an informed decision about whether or not to use the biomedical laser device for the at least one of: the new medical procedure, the new medical treatment, the activation of the new drug, the illumination of the new dye.

Optionally, a given notification is one of: an audio notification, a visual notification, an audio-visual notification, a text notification, an image notification. In an example, the given notification is an audio notification, wherein a first audio indicates the successful reconfiguration of the biomedical laser device and a second audio indicates the unsuccessful reconfiguration of the biomedical laser device. In another example, the given notification is a visual notification, wherein blinking of a green light-emitting diode (LED) indicates the successful reconfiguration of the biomedical laser device and blinking of a red LED indicates the unsuccessful reconfiguration of the biomedical laser device.

Optionally, the method according to the first aspect, further comprises:
collecting, from the biomedical laser device, information indicative of a current geographical location of the biomedical laser device;
accessing, from a database, information pertaining to light output properties required for a plurality of medical procedures, medical treatments, drugs or dyes that are permitted for use in the current geographical location of the biomedical laser device; and
selecting, from amongst the plurality of medical procedures, medical treatments, drugs or dyes, at least one medical procedure, medical treatment, drug or dye whose required light output properties match the measured light output properties of the biomedical laser device, wherein the step of determining the new set of operational parameters is performed based on the light output properties required for the at least one medical procedure, medical treatment, drug or dye.

Optionally, the step of collecting the information indicative of the current geographical location of the biomedical laser device is performed periodically.

Optionally, the information indicative of the current geographical location of the biomedical laser device comprises geographical location data of the biomedical laser device. Optionally, the geographical location data of the biomedical laser device comprises at least latitude coordinates and longitude coordinates of the biomedical laser device.

In an embodiment, the biomedical laser device comprises a location sensor for determining the geographical location data of the biomedical laser device. Optionally, in this regard, the location sensor is implemented as at least one of: a Global Positioning System (GPS) receiver, a Global Navigation Satellite System (GNSS) receiver. Optionally, the location sensor is coupled to the processor.

In another embodiment, geographical location data of the biomedical laser device is obtained by Internet Protocol (IP) address look up. IP address look up involves determining geolocation of the biomedical laser device, based on IP address of the biomedical laser device. The IP address is assigned either to the biomedical laser device, or to the computing device coupled to the biomedical laser device.

In yet another embodiment, the geographical location data of the biomedical laser device is obtained from registration data of the biomedical laser device. The registration data of the biomedical laser device may be stored at the database coupled to the server arrangement or at the processor of the biomedical laser device, and may comprise identification (ID), and other information related to the biomedical laser device. For example, the ID of the biomedical laser device can be associated with sales data or installation data comprising address, room and the like, of the biomedical laser device.

Optionally, the geographical location data of the biomedical laser device is used to extract a setting data associated with the biomedical laser device and the current geographical location of the biomedical laser device. The setting data can be for example that a biomedical laser device in non-hospital environment cannot be used for medical purposes. The setting data can be used to provide the set of operational parameters, and also the new set of operational parameters when the biomedical laser device is re-configured.

Optionally, the database is coupled in communication with the server arrangement. Herein, the term "database" generally refers to hardware, software, firmware, or a combination of these for storing data in an organized (namely, structured) manner, thereby, allowing for easy storage, access (namely, retrieval), updating and analysis of such data. The term "database" also encompasses database servers that provide the aforesaid database services to the system.

Optionally, the database is configured to store information pertaining to light output properties required for a plurality of medical procedures, medical treatments, drugs or dyes that are permitted for use in a plurality of geographical locations of the biomedical laser device. By optionally accessing the database, the server arrangement checks which medical procedures, medical treatments, drugs or dyes are permitted for use in the current geographical location of the biomedical laser device.

Optionally, the selection of the at least one medical procedure, medical treatment, drug or dye is based upon the measured light output properties of the biomedical laser device. In other words, only that at least one medical procedure, medical treatment, drug or dye, which can be employed with the currently available output parameter space of the biomedical laser device, is selected from amongst the plurality of medical procedures, medical treatments, drugs or dyes.

Optionally, the new set of operational parameters are determined based on the light output properties required for the at least one medical procedure, medical treatment, drug or dye, as the new set of operational parameters are to be employed for the at least one medical procedure, medical treatment, drug or dye.

Optionally, the method according to the first aspect further comprises: identifying a person using the biomedical laser device; extracting, from the database or the memory module, a profile data of the person; providing the set of operational parameters based on the profile data; and determining the new set of operational parameters based on the profile data. Optionally, the method according to the first aspect further comprises: obtaining product information of the biomedical laser device; extracting, from the database, an operational data associated with the product information; providing the set of operational parameters based on the operational data; and determining the new set of operational parameters based on the operational data.

Optionally, the person using the biomedical laser device can be identified for example by a username and a password, or a smart card. The database of the server arrangement can be configured to have a profile data of the person, such as what operational modes the person is allowed to have access to and use (for example based on specialty of a doctor operating the biomedical laser device).

Optionally, the product information of the biomedical laser device is scanned information related to a drug used by a patient. The scanned information can be a bar code of the medicine package or a radio frequency identifier (RFID) of the medicine package. Optionally, the product information is related to any exchangeable part or additional part of the biomedical laser device (for example, such as an optical head). The product information may be used to extract from the database the operational data associated with the product information and providing the new set of operational parameters based on the operational data. As an example, if the drug used by patient limits the range of power and wavelengths which can be used for biomedical treatments, that product information (of the used drug) can trigger the new set of operational parameters for the biomedical laser device. Alternatively, when for example a new configuration of the biomedical laser device (obtaining a new set of product information) is obtained, this can be used to further extract a new set of operational data and further provide the new set of operational parameters to the biomedical laser device.

Additionally, the method according to the first aspect further comprises obtaining ambient temperature around the biomedical laser device using a temperature sensor or external source (such as room temperature sensor of office/home automation system). The biomedical laser device might have a range of approved ambient temperature ranges. The approved ambient temperature ranges are typically defined in the biomedical laser device acceptance specification. The ambient temperature can be used as an additional parameter to determine operational modes of the biomedical laser device. As an example, if the ambient temperature is outside of safe operational margin, the given operational mode may be changed to the new operational mode, to prohibit usage of the biomedical laser device totally or for certain biomedical applications. The term "ambient temperature" can be understood broadly to refer to external or internal temperatures of the biomedical laser device.

Next, there will be described some components of the biomedical laser device in more detail.

Optionally, the laser light emitter comprises at least one light emitting element, such as a light emitting circuit, wherein the processor is configured to control the at least one light emitting circuit to emit laser light of at least one target wavelength. In an example, the laser light emitter of the biomedical laser device may be operated to emit monochromatic light at a target wavelength of 632 nanometer for activating a specific drug or dye molecule in photodynamic therapy application. In such an example, optionally, the same laser light emitter may be operated to emit monochromatic light at a target wavelength of 635 nanometer for activating another drug or dye molecule in photodynamic therapy. In another example, a first light emitting circuit of the laser light emitter may be operated to emit monochromatic light at a target wavelength of 532 nanometer for activating a fluorescent dye in a gene sequencing application, whereas a second light emitting circuit of the laser light emitter may be operated to emit a second wavelength of 660 nm for activating another set of fluorescent dyes in a gene sequencing application, and the second light emitting circuit may be activated for use at a later period of time also remotely. The biomedical laser device can comprise a plurality of light emitting circuits. The light emitting circuits may be operated to emit monochromatic light with same or different target wavelengths. The circuits might be independently operated from each other. For example, the first light emitting circuit might emit a target wavelength of 532 nanometers and the second light emitting circuit might emit another target wavelength of 660 nanometers. As another example, the first light emitting circuit might provide laser light continuously and the second might provide it in pulsed matter during an operational mode.

Optionally, the laser light emitter is arranged in a laser component module. The laser component module beneficially provides a casing (or a protective housing) for the laser light emitter. Furthermore, the laser component module may beneficially prevent leakage of the emitted laser light produced by the laser light emitter, into an environment (namely surrounding) of use of the biomedical laser device. Optionally, the laser component module comprises a cylindrical body coaxially disposed with a direction of emission of the emitted laser light, in a manner that the laser component module completely encloses the laser light emitter. In such an instance, the laser component module may be arranged so as not to interfere (or obstruct) an optical path of the emitted laser light produced by the laser light emitter. Optionally, the laser component module comprises an opening at a surface thereof to allow the light guide to pass through. In such an instance, dimensions of the light guide and the opening may be such that the emitted laser light does not leak into the environment of use of the biomedical laser device.

Throughout the present disclosure, the term "light guide" refers to equipment configured to allow passage of light therethrough. In an embodiment, the light guide is an optical fibre cable. In another embodiment, the light guide is an optical waveguide. The light guide may be optically coupled to the laser light emitter by way of the light coupling arrangement. In such an embodiment, the at least a part of the light guide may lie within the laser component module. As mentioned previously, one end of the light guide is coupled with the light coupling arrangement, and the other end of the light guide is used to administer the emitted laser light for the purpose of one or more biomedical applications. Furthermore, the light guide can comprise an optical head i.e. a contained space, where a collimated laser beam can travel and be further manipulated. The optical head can be arranged at an end of the light guide such as optical fibre. The optical head can be used to modify light from the laser light emitter for example with a lenses system, collimators, splitters, actuating prims/mirrors used in scanning function etc. The processor can be configured to control the optical head. Controlling of the optical head can be considered to be an operational parameter. The fourth sensor can be used for example to detect operation of the scanning function.

The light coupling arrangement is disposed inside the laser component module. The light coupling arrangement is configured to provide a coupling arrangement between the laser light emitter and the light guide. In an embodiment, the light coupling arrangement detachably couples the laser light emitter and the light guide. Optionally, the light coupling arrangement is a device that provides a leak proof connection between the laser light emitter and the light guide.

The present disclosure also relates to the system as described above. Various embodiments and variants disclosed above, with respect to the aforementioned first aspect, apply mutatis mutandis to the system.

Optionally, the server arrangement is further configured to:
  collect, from the biomedical laser device, information indicative of a current geographical location of the biomedical laser device;
  access, from a database, information pertaining to light output properties required for a plurality of medical procedures, medical treatments, drugs or dyes that are permitted for use in the current geographical location of the biomedical laser device;
  select, from amongst the plurality of medical procedures, medical treatments, drugs or dyes, at least one medical procedure, medical treatment, drug or dye whose required light output properties match the measured light output properties of the biomedical laser device; and
  determine the new set of operational parameters based on the light output properties required for the at least one medical procedure, medical treatment, drug or dye.

Optionally, the server arrangement is configured to store, at the database, data and/or information exchanged with the processor of the biomedical laser device. Optionally, the server arrangement is configured to store, at the database, historical operation data of at least one biomedical laser device communicably coupled thereto. Beneficially, storing at least one of: the data and/or information exchanged with the processor of the biomedical laser device, the historical operation data of at least one biomedical laser device, facilitates re-configuration of the biomedical laser device for a new biomedical application. Moreover, such stored data and/or information may facilitate at least one learning algorithm to derive the new operational mode of the biomedical laser device, and activate the new set of operational parameters in use remotely.

Optionally, the server arrangement is further configured to:
  collect, from the biomedical laser device, information indicative of light output properties of the biomedical laser device measured during the new operational mode;

detect whether or not the measured light output properties deviate from predefined light output properties for the new operational mode;

send, to the biomedical laser device, a notification indicating a successful reconfiguration of the biomedical laser device when the measured light output properties do not deviate from the predefined light output properties for the new operational mode; and send, to the biomedical laser device, a notification indicating an unsuccessful reconfiguration of the biomedical laser device when the measured light output properties deviate from the predefined light output properties for the new operational mode.

Optionally, the server arrangement is configured to collect the information indicative of the measured light output properties periodically.

Optionally, in the system, the set of operational parameters comprises at least one of: a target wavelength, a target energy output of laser light emitted during the given operational mode, and wherein the new set of operational parameters comprises at least one of: a new target wavelength, a new target energy output of laser light emitted during the new operational mode.

Optionally, in the system, the measured light output properties comprise at least one of: a wavelength, a spectrum, an energy, a pulse energy, an optical power, a pulse form factor of laser light emitted during the given operational mode, and wherein the predefined light output properties comprise at least one of: a reference wavelength, a reference range of wavelengths, a reference spectrum, a reference range of spectrum, a reference energy, a reference range of energies, a reference pulse energy, a reference range of pulse energies, a reference optical power, a reference range of optical powers, a reference pulse form factor, a reference range of pulse form factors predefined for laser light emitted during the given operational mode.

It will be appreciated that the server arrangement allows for centralized monitoring and re-configuration of at least one biomedical laser device communicably coupled thereto. Furthermore, optionally, the server arrangement allows for configuring and controlling operation of the at least one biomedical laser device in at least one geographical location. Herein, "configuring" encompasses both pre-configuration and re-configuration.

Optionally, the server arrangement is further configured to provide a web interface to access information related to biomedical laser devices.

The present disclosure also relates to the method according to the third aspect (described above). Various embodiments and variants disclosed above, with respect to the aforementioned first and second aspects, apply mutatis mutandis to the method according to the third aspect.

The method according to the third aspect is implemented by the biomedical laser device. Optionally, the method according to the third aspect is implemented by the processor of the biomedical laser device.

Optionally, the communication module of the processor is configured to communicate with the server arrangement for exchanging (namely, sending and receiving) data and/or information with the server arrangement. Optionally, the memory module of the processor is configured to store the data and/or information exchanged with the server arrangement. Locally stored data and/or information at the memory module may be easily accessed by the trained biomedical practitioner or operator. Such data and/or information may be further utilized to facilitate biomedical research.

Examples of the memory module, include but are not limited to, random access memory, hard disk drive, flash memory and optical disc.

Optionally, measuring the light output properties of the biomedical laser device during the given operational mode comprises obtaining the sensor data measured by the light sensing arrangement during the given operational mode.

Optionally, the light sensing arrangement comprises at least one of:
a first light sensor arranged in a laser component module;
a second light sensor arranged in proximity of the light guide;
a third light sensor arranged at an end of the light guide; and
a fourth light sensor arranged in an optical head.

Optionally, the biomedical laser device comprises the light sensing arrangement. Optionally, the processor of the biomedical laser device is communicably coupled to the light sensing arrangement. The processor obtains the sensor data measured by the light sensing arrangement. Optionally, sensors of the light sensing arrangement automatically send sensor data to the processor.

Optionally, the light sensing arrangement is configured to measure light output properties of the biomedical laser device. Optionally, information indicative of measured light output properties of the biomedical laser device during an operational mode comprises measured sensor data from the first light sensor, the second light sensor, the third light sensor, and the fourth light sensor, during the operational mode. Optionally, the light sensing arrangement measures intensity of ambient light. The intensity of ambient light is also indicative of light output properties of the biomedical laser device during the operational mode.

Optionally, the laser light emitted by the biomedical laser device is incident on light-sensitive elements of the first light sensor, the second light sensor, the third light sensor, and the fourth light sensor. The aforesaid arrangement of the first light sensor, the second light sensor, the third light sensor, and the fourth light sensor, measures the light output properties at multiple positions within the biomedical laser device, thereby allowing for detection of dissimilarities in the light output properties that may occur at the multiple positions. It is also possible to arrange less or more than four light sensors, such as one, two, three, five, six or seven light sensors in the light sensing arrangement. For example, the light sensing arrangement may comprise the first sensor and the second sensor, the first sensor and the third sensor, or the third sensor and the fourth sensor. Likewise, it may comprise the first, second and third sensors; the first, second and fourth sensor; and the like. By the term "proximity" it is meant a position where the light emitted can effectively be measured.

In an exemplary implementation, the first light sensor may be arranged in the laser component module to measure ambient light within the laser component module. The laser component module may include the laser light emitter arranged therein, wherein the laser light emitter may be optically coupled to the light guide via the light coupling arrangement. In such an instance, at least a part of the light guide may lie within the laser component module. Therefore, the first light sensor may be operable to measure intensity (or energy) of the ambient light that results from at least one of: leakage of the laser light emitted from the laser light emitter, leakage of the laser light emitted from the light coupling arrangement, leakage of the laser light emitted from the part of the light guide within the laser component module, leakage of the laser light emitted from an interface between the laser light emitter and the light coupling arrangement and leakage of the laser light emitted from an interface between the light coupling arrangement and the light guide. It will be appreciated that in this regard, a high value of measured intensity of the ambient light indicates a high magnitude of leakage of the emitted laser light, which may be undesirable.

Furthermore, in such an exemplary implementation, the second light sensor may be arranged in proximity of the light guide to measure the energy of the emitted laser light that may leak from the light guide. In such an instance, the second light sensor may be attached, for example, to the light guide. Moreover, in such an exemplary implementation, the third light sensor may be arranged at an end of the light guide, from which the emitted laser light may be administered for the purpose of biomedical applications. In such an instance, the third light sensor may be configured to measure the wavelength and the energy of the emitted laser light. Furthermore, in the exemplary implementation, the fourth light sensor may be arranged in the optical head. The optical head is a component or element that might be optionally arranged at the end of the light guide. The optical head and the fourth sensor can be thus configured to a contained space, where a collimated laser beam can travel and be further manipulated and monitored.

In an embodiment, the first light sensor, the second light sensor, the third light sensor and the fourth sensor are same kind of sensor. For example, the first light sensor, the second light sensor, the third light sensor and the fourth light sensor may be configured to measure the intensity of emitted laser light. In such example, the first light sensor, the second light sensor, the third light sensor and the fourth light sensor may be a photoresistor, a photo diode, or the like. In another embodiment, the first light sensor, the second light sensor, the third light sensor and the fourth light sensor are a combination of different kinds of sensors. For example, the first light sensor and the second light sensor may be configured to measure the intensity of the emitted laser light and the third light sensor may be configured to measure the wavelength of the emitted laser light. In such example, the first sensor and the second sensor may be a photoresistor, a photo diode, or the like, and the third sensor may be a wavemeter or a spectrometer. Optionally, the first light sensor is detachably coupled inside the light coupling arrangement. Additionally, the second light sensor may be affixed to the light guide. More optionally, the third light sensor may be placed such that the emitted laser light is incident upon light-sensitive elements of the third light sensor. More optionally, the fourth light sensor may be placed such that it can measure light inside of the optical head.

By sending, to the server arrangement, the information indicative of the measured light output properties for the given operational mode, accurate remote monitoring of the biomedical laser device is facilitated.

Optionally, the method according to the third aspect further comprises sending, to the server arrangement, information indicative of a current geographical location of the biomedical laser device. Optionally, the processor is configured to obtain, from the location sensor, the determined geographical location data of the biomedical laser device, prior to sending said information to the server arrangement.

Optionally, the method according to the third aspect further comprises:
measuring light output properties of the biomedical laser device during the new operational mode;
sending, to the server arrangement, information indicative of the measured light output properties for the new operational mode; and
receiving, from the server arrangement, a notification indicating whether the reconfiguration of the biomedical laser device is successful or unsuccessful.

Optionally, measuring the light output properties of the biomedical laser device during the new operational mode comprises obtaining the sensor data measured by the light sensing arrangement during the new operational mode.

Optionally, upon receiving the notification indicating whether the reconfiguration of the biomedical laser device is successful or unsuccessful, the processor is configured to present the notification at any of: the computing device coupled to the biomedical laser device, a device associated with the biomedical laser device, a device associated with the user of the biomedical laser device.

Optionally, in the method according to the third aspect, the steps of measuring light output properties and sending the information indicative of the measured light output properties are performed periodically. In this way, the processor facilitates the server arrangement to remotely monitor the biomedical laser device periodically. It will be appreciated that periodic time intervals for performing said steps may be equal time intervals or unequal time intervals.

Optionally, in the method according to the third aspect, the set of operational parameters comprises at least one of: a target wavelength, a target energy output of laser light emitted during the given operational mode, and wherein the new set of operational parameters comprises at least one of: a new target wavelength, a new target energy output of laser light emitted during the new operational mode.

Optionally, in the method according to the third aspect, the measured light output properties comprise at least one of: a wavelength, a spectrum, an energy, a pulse energy, an optical power, a pulse form factor of laser light emitted during the given operational mode, and wherein the predefined light output properties comprise at least one of: a reference wavelength, a reference range of wavelengths, a reference spectrum, a reference range of spectrum, a reference energy, a reference range of energies, a reference pulse energy, a reference range of pulse energies, a reference optical power, a reference range of optical powers, a reference pulse form factor, a reference range of pulse form factors predefined for laser light emitted during the given operational mode.

Optionally, the processor is further configured to measure an operational response of the biomedical laser device in the given operational mode and/or the new operational mode. The "operational response" of the biomedical laser device refers to a variation in operating characteristics of the biomedical laser device, whilst the biomedical laser device is operated in a specific operational mode. Optionally, measuring the operational response of the biomedical laser device comprises measuring at least one of: a voltage transient as a function of time, a current transient as a function of time, a temperature of the laser light emitter, a power usage of the biomedical laser device during operation. Furthermore, it will be appreciated that the operational response is measured by employing measuring instruments such as voltage meters, current meters, thermometers, and the like. As an example, the voltage transient (namely voltage fluctuations within the laser light emitter) and the current transient (namely current fluctuations within the laser light emitter) may be measured as a function of time, to constitute measured operational response of the biomedical laser device. In such an example, the processor may record variation of the current input and the voltage input with regard to time to detect and measure the current and voltage transients respectively.

Optionally, the operational response of the biomedical laser device is measured during an entire time duration of operation thereof. Alternatively, optionally, the operational response of the biomedical laser device is measured during at least a part of the entire time duration of operation of the biomedical laser device.

In an embodiment, the processor is further configured to: analyse the measured operational response of the biomedical laser device in the given operational mode and/or the new operational mode; and trigger an action, based on the analysis. Such analysis is performed for identifying undesired errors (namely, faults) in operation of the biomedical laser device, optionally, to predict possible future occurrence of the undesired errors. Beneficially, such analysis facilitates prompt and timely control of the biomedical laser device. Optionally, the analysis of the operational response of the biomedical laser device comprises comparing the measured operational response with a predefined operational response. Presence of significant deviation between the measured operational response and the predefined operational response is indicative of faulty/undesirable operation of the biomedical laser device. Herein, the "action" refers to an act or an event that is undertaken for controlling the biomedical laser device, to operate the biomedical laser device normally. Optionally, the action pertains to at least one of: implementation of corrective measures in an event of faulty operation of the biomedical laser device, discontinuing use of the biomedical laser device, re-configuring the biomedical laser device for a different operational mode, using the biomedical laser device for a limited operational mode, implementation of biomedical research by employing the analysis of the biomedical laser device. As an example, the action may be implementation of a corrective measure such as a maintenance procedure for the biomedical laser device. The maintenance procedure may involve repair and/or replacement of at least one component of the biomedical laser device and may be carried out by a trained maintenance person or the user of the biomedical laser device.

In another embodiment, the processor is further configured to: send, to the server arrangement, the measured operational response of the biomedical laser device in the given operational mode and/or the new operational mode; and receive, from the server arrangement, a notification indicating the action to be triggered. In such a case, the server arrangement performs the analysis of the measured operational response of the biomedical laser device and triggers the action, based on the analysis.

Optionally, the processor is further configured to: facilitate pre-configuration of a second biomedical laser device, based on historical operation data of a first biomedical laser device.

DETAILED DESCRIPTION OF THE DRAWINGS

Referring to FIG. 1, illustrated are steps of a method for re-configuring a biomedical laser device, in accordance with an embodiment of the present disclosure. This method is performed by a system for re-configuring the biomedical laser device, wherein the system comprises a server arrangement coupled in communication with the biomedical laser device. The biomedical laser device is pre-configured to be operable in one or more operational modes. The biomedical laser device is provided with a set of operational parameters to be employed in a given operational mode of the one or more operational modes, wherein the set of operational parameters are employed for at least one of: a given medical procedure, a given medical treatment, an activation of a given drug, an illumination of a given dye. At step 102, information indicative of light output properties of the biomedical laser device measured during the given operational mode is collected from the biomedical laser device. At step 104, a deviation in the measured light output properties with respect to predefined light output properties for the given operational mode is detected. At step 106, a new set of operational parameters is determined based on the detected deviation. The new set of operational parameters are to be employed for at least one of: a new medical procedure, a new medical treatment, an activation of a new drug, an illumination of a new dye. At step 108, the new set of operational parameters is sent to the biomedical laser device for re-configuring the biomedical laser device to be operable in a new operational mode, wherein the new set of operational parameters are employed in the new operational mode.

The steps 102, 104, 106, and 108 are only illustrative and other alternatives can also be provided where one or more steps are added, one or more steps are removed, or one or more steps are provided in a different sequence without departing from the scope of the claims herein.

Figure 2:
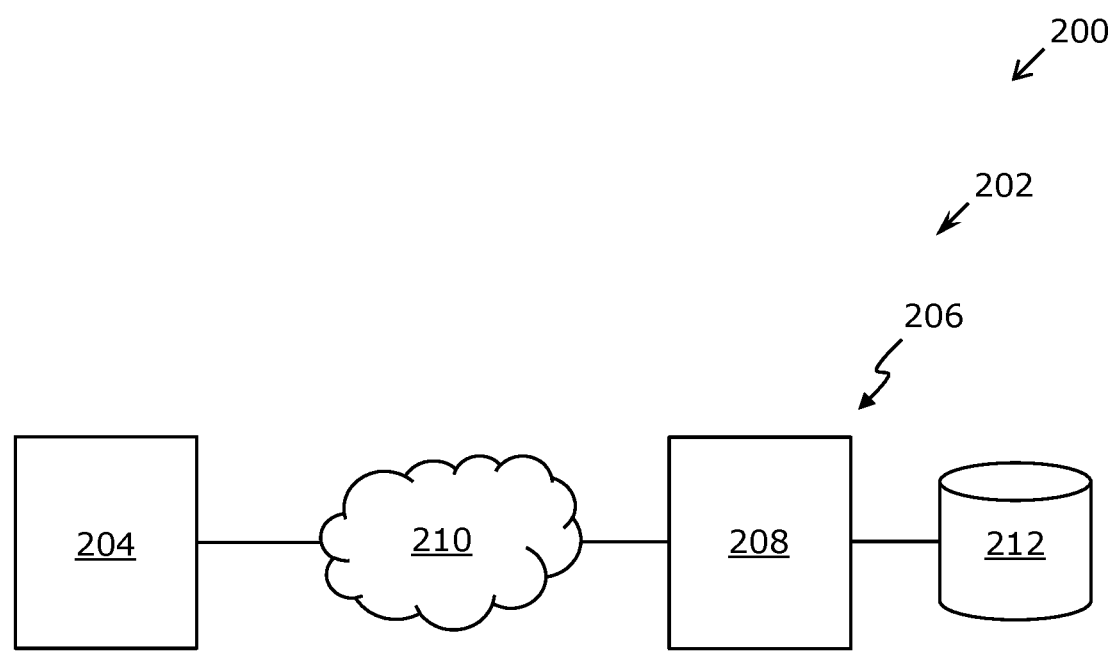
FIG. 2 is a schematic illustration of an exemplary environment wherein a system for re-configuring a biomedical laser device is used, in accordance with an embodiment of the present disclosure.

Referring to FIG. 2, illustrated is a schematic illustration of an exemplary environment 200 wherein a system 202 for re-configuring a biomedical laser device 204 is used, in accordance with an embodiment of the present disclosure. The system 202 comprises a server arrangement 206 coupled in communication with the biomedical laser device 204. The server arrangement 206 is shown to be implemented a single server 208. The biomedical laser device 204 is shown to be coupled in communication with the server arrangement 206 via a communication network 210. The server arrangement 206 is optionally also coupled in communication with a database 212.

It may be understood by a person skilled in the art that the FIG. 2 is merely an example for sake of clarity, which should not unduly limit the scope of the claims herein. The person skilled in the art will recognize many variations, alternatives, and modifications of embodiments of the present disclosure.

Figure 3:
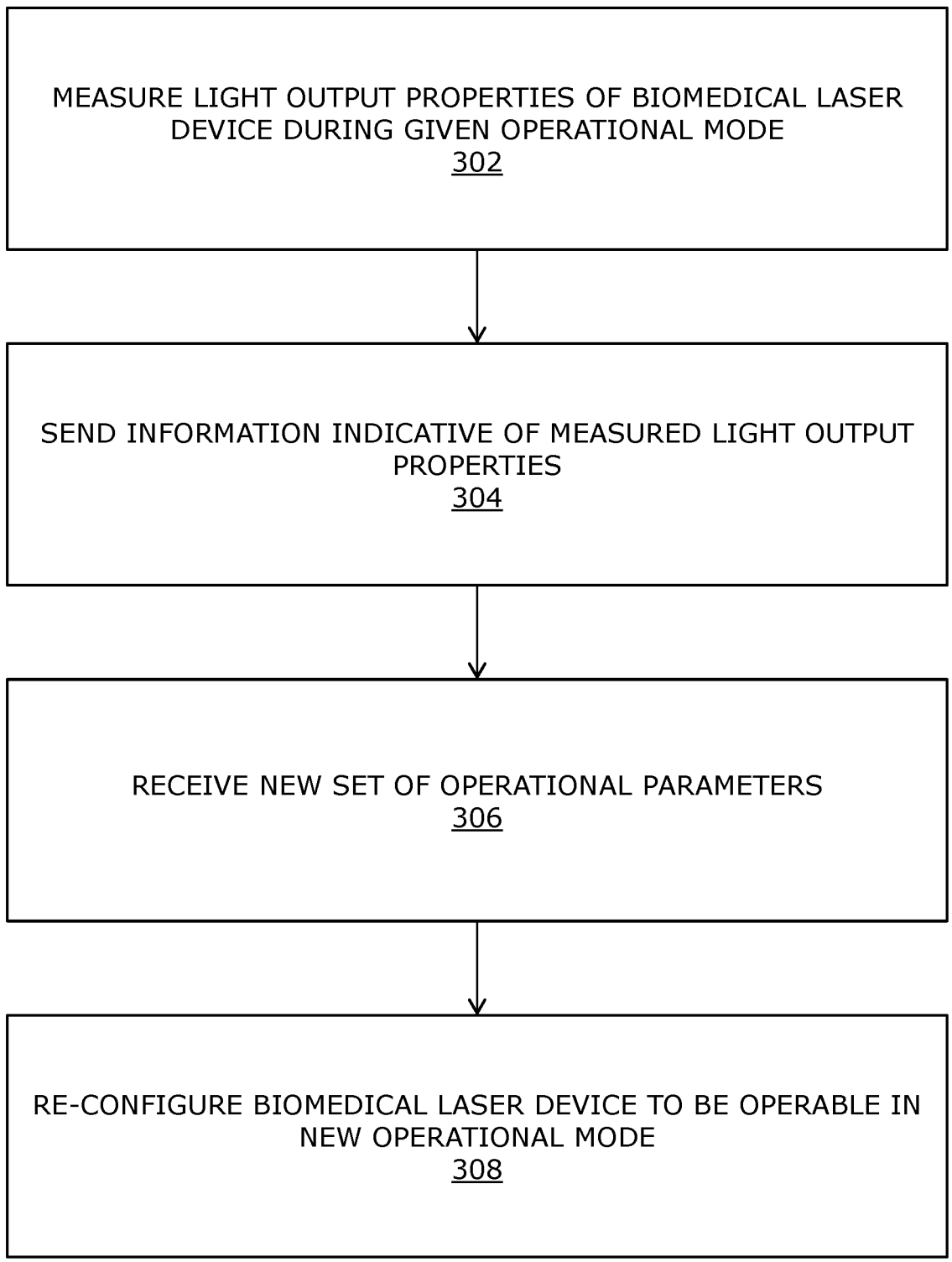
FIG. 3 illustrates steps of a method for re-configuring a biomedical laser device, in accordance with an embodiment of the present disclosure.

Referring to FIG. 3, illustrated are steps of a method for re-configuring a biomedical laser device, in accordance with an embodiment of the present disclosure. This method is performed by a processor of the biomedical laser device. The biomedical laser device is pre-configured to be operable in one or more operational modes. The biomedical laser device is provided with a set of operational parameters to be employed in a given operational mode of the one or more operational modes, wherein the set of operational parameters are employed for at least one of: a given medical procedure, a given medical treatment, an activation of a given drug, an illumination of a given dye. At step 302, light output properties of the biomedical laser device during the given operational mode are measured. At step 304, information indicative of the measured light output properties for the given operational mode is sent to a server arrangement. At step 306, a new set of operational parameters that are to be employed for at least one of: a new medical procedure, a new medical treatment, an activation of a new drug, an illumination of a new dye, is received from the server arrangement. At step 308, the biomedical laser device is re-configured to be operable in a new operational mode, wherein the new set of operational parameters are employed in the new operational mode.

The steps 302, 304, 306, and 308 are only illustrative and other alternatives can also be provided where one or more steps are added, one or more steps are removed, or one or more steps are provided in a different sequence without departing from the scope of the claims herein.

Figure 4:
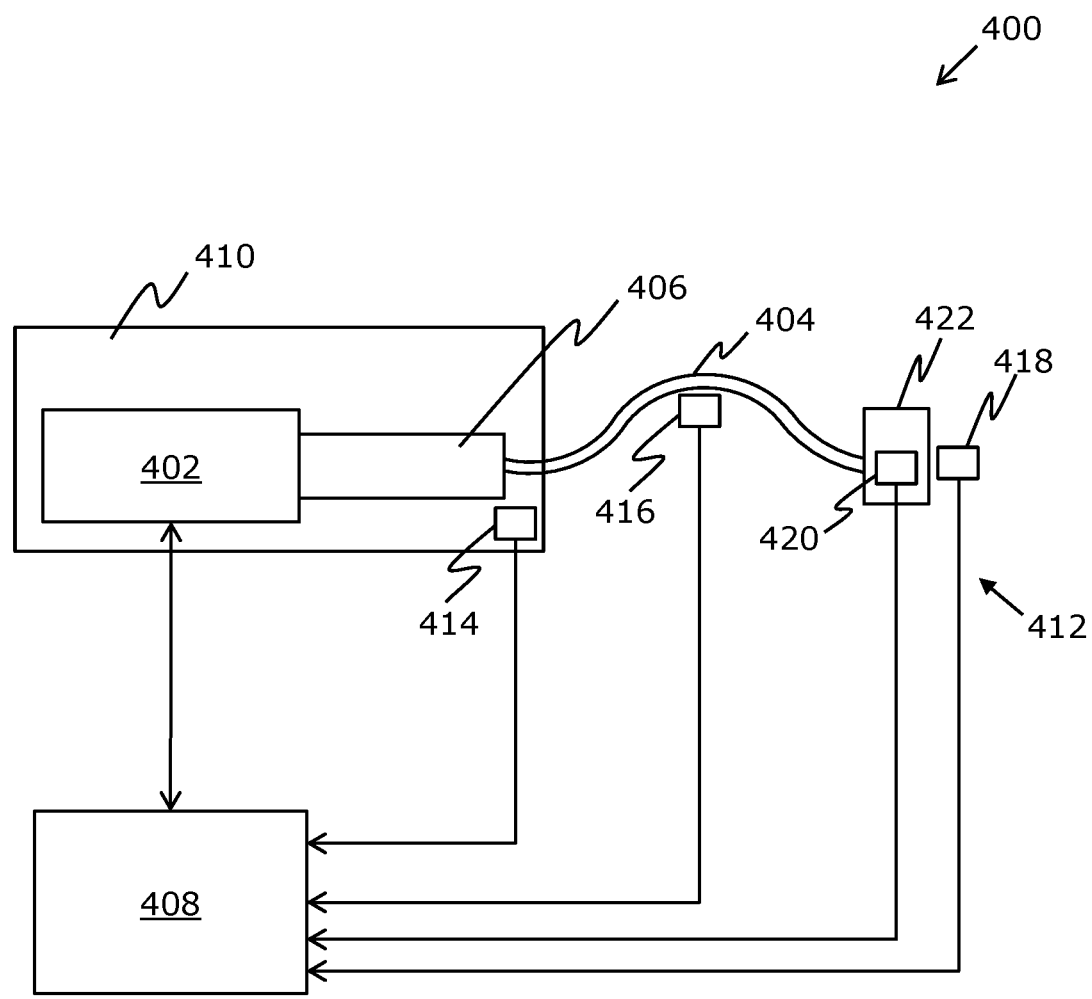
FIG. 4 is a schematic illustration of a biomedical laser device, in accordance with an embodiment of the present disclosure.

Referring to FIG. 4, illustrated is a biomedical laser device 400, in accordance with an embodiment of the present disclosure. The biomedical laser device 400 comprises a laser light emitter 402 for emitting laser light, a light guide 404 optically coupled to the laser light emitter 402 via a light coupling arrangement 406, and a processor 408 coupled to the laser light emitter 402. The laser light emitter 402 is arranged in a laser component module 410. The biomedical laser device 400 further comprises a light sensing arrangement 412 configured to measure light output properties of the biomedical laser device 400. The light sensing arrangement 412 is communicably coupled to the processor 408. In the illustrated embodiment, the light sensing arrangement 412 is shown to comprise a first light sensor 414, a second light sensor 416, a third light sensor 418, and a fourth light sensor 420. The first light sensor 414 is arranged in the laser component module 410. The second light sensor 416 is arranged in proximity of the light guide 404. The third light sensor 418 is arranged at an end of the light guide 404. The fourth light sensor 420 is arranged in an optical head 422, wherein the light guide 404 comprises the optical head 422.

It may be understood by a person skilled in the art that the FIG. 4 is merely an example for sake of clarity, which should not unduly limit the scope of the claims herein. The person skilled in the art will recognize many variations, alternatives, and modifications of embodiments of the present disclosure. For example, the light sensing arrangement 412 may comprise only the first light sensor 414, the second light sensor 416, and the third light sensor 418.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A method for re-configuring a biomedical laser device, wherein the biomedical laser device is pre-configured to be operable in one or more operational modes, the biomedical laser device being provided with a set of operational parameters to be employed in a given operational mode of the one or more operational modes, wherein the set of operational parameters are employed for at least one of: a given medical procedure, a given medical treatment, an activation of a given drug, an illumination of a given dye, the method comprising:

collecting, from the biomedical laser device, information indicative of light output properties of the biomedical laser device measured during the given operational mode;

detecting a deviation in the measured light output properties with respect to predefined light output properties for the given operational mode;

determining, based on the detected deviation, a new set of operational parameters that are to be employed for at least one of: a new medical procedure, a new medical treatment, an activation of a new drug, an illumination of a new dye; and sending the new set of operational parameters to the biomedical laser device for re-configuring the biomedical laser device to be operable in a new operational mode, wherein the new set of operational parameters are employed in the new operational mode.

2. The method of claim 1, further comprising:

collecting, from the biomedical laser device, information indicative of a current geographical location of the biomedical laser device;

accessing, from a database, information pertaining to light output properties required for a plurality of medical procedures, medical treatments, drugs or dyes that are permitted for use in the current geographical location of the biomedical laser device; and selecting, from amongst the plurality of medical procedures, medical treatments, drugs or dyes, at least one medical procedure, medical treatment, drug or dye whose required light output properties match the measured light output properties of the biomedical laser device, wherein the step of determining the new set of operational parameters is performed based on the light output properties required for the at least one medical procedure, medical treatment, drug or dye.

3. The method of claim 1, further comprising:

collecting, from the biomedical laser device, information indicative of light output properties of the biomedical laser device measured during the new operational mode;

detecting whether or not the measured light output properties deviate from predefined light output properties for the new operational mode;

sending, to the biomedical laser device, a notification indicating a successful reconfiguration of the biomedical laser device when the measured light output properties do not deviate from the predefined light output properties for the new operational mode; and sending, to the biomedical laser device, a notification indicating an unsuccessful reconfiguration of the biomedical laser device when the measured light output properties deviate from the predefined light output properties for the new operational mode.

4. The method of claim 1, wherein the step of collecting the information indicative of the measured light output properties is performed periodically.

5. The method of claim 1, wherein the set of operational parameters comprises at least one of: a target wavelength, a target energy output of laser light emitted during the given operational mode, and wherein the new set of operational parameters comprises at least one of: a new target wavelength, a new target energy output of laser light emitted during the new operational mode.

6. The method of claim 1, wherein the measured light output properties comprise at least one of: a wavelength, a spectrum, an energy, a pulse energy, an optical power, a pulse form factor of laser light emitted during the given operational mode, and wherein the predefined light output properties comprise at least one of: a reference wavelength, a reference range of wavelengths, a reference spectrum, a reference range of spectrum, a reference energy, a reference range of energies, a reference pulse energy, a reference range of pulse energies, a reference optical power, a reference range of optical powers, a reference pulse form factor, a reference range of pulse form factors predefined for laser light emitted during the given operational mode.

7. A system for re-configuring a biomedical laser device, the system comprising a server arrangement coupled in communication with the biomedical laser device, wherein the biomedical laser device is pre-configured to be operable in one or more operational modes, the biomedical laser device being provided with a set of operational parameters to be employed in a given operational mode of the one or more operational modes, wherein the set of operational parameters are to be employed for at least one of: a given medical procedure, a given medical treatment, an activation of a given drug, an illumination of a given dye, wherein the server arrangement is configured to:
- collect, from the biomedical laser device, information indicative of light output properties of the biomedical laser device measured during the given operational mode;
- detect a deviation in the measured light output properties with respect to predefined light output properties for the given operational mode;
- determine, based on the detected deviation, a new set of operational parameters that are to be employed for at least one of: a new medical procedure, a new medical treatment, an activation of a new drug, an illumination of a new dye; and
- send the new set of operational parameters to the biomedical laser device for re-configuring the biomedical laser device to be operable in a new operational mode, wherein the new set of operational parameters are to be employed in the new operational mode.

8. The system of claim 7, wherein the server arrangement is further configured to:
- collect, from the biomedical laser device, information indicative of a current geographical location of the biomedical laser device;
- access, from a database, information pertaining to light output properties required for a plurality of medical procedures, medical treatments, drugs or dyes that are permitted for use in the current geographical location of the biomedical laser device;
- select, from amongst the plurality of medical procedures, medical treatments, drugs or dyes, at least one medical procedure, medical treatment, drug or dye whose required light output properties match the measured light output properties of the biomedical laser device; and
- determine the new set of operational parameters based on the light output properties required for the at least one medical procedure, medical treatment, drug or dye.

9. The system of claim 7, wherein the server arrangement is further configured to:
- collect, from the biomedical laser device, information indicative of light output properties of the biomedical laser device measured during the new operational mode;
- detect whether or not the measured light output properties deviate from predefined light output properties for the new operational mode;
- send, to the biomedical laser device, a notification indicating a successful reconfiguration of the biomedical laser device when the measured light output properties do not deviate from the predefined light output properties for the new operational mode; and
- send, to the biomedical laser device, a notification indicating an unsuccessful reconfiguration of the biomedical laser device when the measured light output properties deviate from the predefined light output properties for the new operational mode.

10. The system of claim 7, wherein the server arrangement is configured to collect the information indicative of the measured light output properties periodically.

11. The system of claim 7, wherein the set of operational parameters comprises at least one of: a target wavelength, a target energy output of laser light emitted during the given operational mode, and wherein the new set of operational parameters comprises at least one of: a new target wavelength, a new target energy output of laser light emitted during the new operational mode.

12. The system of claim 7, wherein the measured light output properties comprise at least one of: a wavelength, a spectrum, an energy, a pulse energy, an optical power, a pulse form factor of laser light emitted during the given operational mode, and wherein the predefined light output properties comprise at least one of: a reference wavelength, a reference range of wavelengths, a reference spectrum, a reference range of spectrum, a reference energy, a reference range of energies, a reference pulse energy, a reference range of pulse energies, a reference optical power, a reference range of optical powers, a reference pulse form factor, a reference range of pulse form factors predefined for laser light emitted during the given operational mode.

13. A method for re-configuring a biomedical laser device, wherein the biomedical laser device is pre-configured to be operable in one or more operational modes, the biomedical laser device being provided with a set of operational parameters to be employed in a given operational mode of the one or more operational modes, wherein the set of operational parameters are employed for at least one of: a given medical procedure, a given medical treatment, an activation of a given drug, an illumination of a given dye, the method comprising:
- measuring light output properties of the biomedical laser device during the given operational mode;
- sending, to a server arrangement, information indicative of the measured light output properties for the given operational mode; and
- receiving, from the server arrangement, a new set of operational parameters that are to be employed for at least one of: a new medical procedure, a new medical treatment, an activation of a new drug, an illumination of a new dye; and
- re-configuring the biomedical laser device to be operable in a new operational mode, wherein the new set of operational parameters are employed in the new operational mode.

14. The method of claim 13, further comprising sending, to the server arrangement, information indicative of a current geographical location of the biomedical laser device.

15. The method of claim 13, further comprising:
- measuring light output properties of the biomedical laser device during the new operational mode;
- sending, to the server arrangement, information indicative of the measured light output properties for the new operational mode; and
- receiving, from the server arrangement, a notification indicating whether the reconfiguration of the biomedical laser device is successful or unsuccessful.

16. The method of claim 13, wherein the steps of measuring light output properties and sending the information indicative of the measured light output properties are performed periodically.

17. The method of claim 13, wherein the set of operational parameters comprises at least one of: a target wavelength, a target energy output of laser light emitted during the given operational mode, and wherein the new set of operational parameters comprises at least one of: a new target wavelength, a new target energy output of laser light emitted during the new operational mode.

18. The method of claim 13, wherein the measured light output properties comprise at least one of: a wavelength, a spectrum, an energy, a pulse energy, an optical power, a pulse form factor of laser light emitted during the given operational mode, and wherein the predefined light output properties comprise at least one of: a reference wavelength, a reference range of wavelengths, a reference spectrum, a reference range of spectrum, a reference energy, a reference range of energies, a reference pulse energy, a reference range of pulse energies, a reference optical power, a reference range of optical powers, a reference pulse form factor, a reference range of pulse form factors predefined for laser light emitted during the given operational mode.

* * * * *